United States Patent [19]

Strong

[11] Patent Number: 4,883,101

[45] Date of Patent: Nov. 28, 1989

[54] FILLING DEVICE WITH SOUND INDICATOR FOR FILLING INJECTION SYRINGE

[75] Inventor: Bernard Strong, Tarzana, Calif.

[73] Assignee: Jordan Enterprises, Garden Grove, Calif.

[21] Appl. No.: 212,210

[22] Filed: Jun. 27, 1988

[51] Int. Cl.⁴ .............................................. B65B 3/32
[52] U.S. Cl. ...................................... 141/27; 141/94; 141/97; 141/98; 141/391; 604/155; 604/187; 604/407
[58] Field of Search ....................... 141/98, 25, 26, 27, 141/329, 330, 94, 391, 97; 604/403, 407, 404, 905, 207, 187, 155, 152; 73/863.01, 863.23, 863.24

[56] References Cited

U.S. PATENT DOCUMENTS

| | | | |
|---|---|---|---|
| 3,844,318 | 10/1974 | Rala et al. | 141/27 |
| 3,935,883 | 2/1976 | Stach et al. | 141/27 |
| 3,965,945 | 6/1976 | Ross | 141/27 |
| 4,252,159 | 2/1981 | Maki | 141/27 |
| 4,346,742 | 8/1982 | Chase et al. | 141/27 X |
| 4,357,971 | 11/1982 | Friedman | 141/27 |
| 4,407,659 | 10/1983 | Adam | 604/155 |
| 4,429,724 | 2/1984 | Dorros et al. | 141/27 |
| 4,434,820 | 3/1984 | Glass | 141/27 X |
| 4,475,915 | 10/1984 | Sloane | 604/414 |
| 4,731,058 | 3/1988 | Doan | 604/155 |

FOREIGN PATENT DOCUMENTS 2166497 5/1986 United Kingdom ............... 604/155

*Primary Examiner*—Ernest G. Cusick
*Attorney, Agent, or Firm*—Willie Krawitz

[57] ABSTRACT

A filling device for filling an injection syringe is provided which enables the user to count the intake dosage by means of a sound indicator which may be mechanical, electrical or an electronic sound device. The filling device includes a movable syringe holder to which is attached a removable syringe that is connectable to a medicinal bottle. The filling device mounts a gear which is movable one gear tooth at a time to actuate a linear gear to which the syringe is mounted. A spring loaded ball bearing is biased against the gear wheel and produces a distinctly audible clicking sound when the gear moves a single notch. These clicking sounds can be counted by a user when the attached syringe holder moves, and hence will accurately indicate the amount of liquid medicine drawn into the syringe. The same device may be connected to a microprocessor controlled voice device to obtain a suitable readout indicating the amount of liquid medicinal uptake by the syringe.

8 Claims, 4 Drawing Sheets

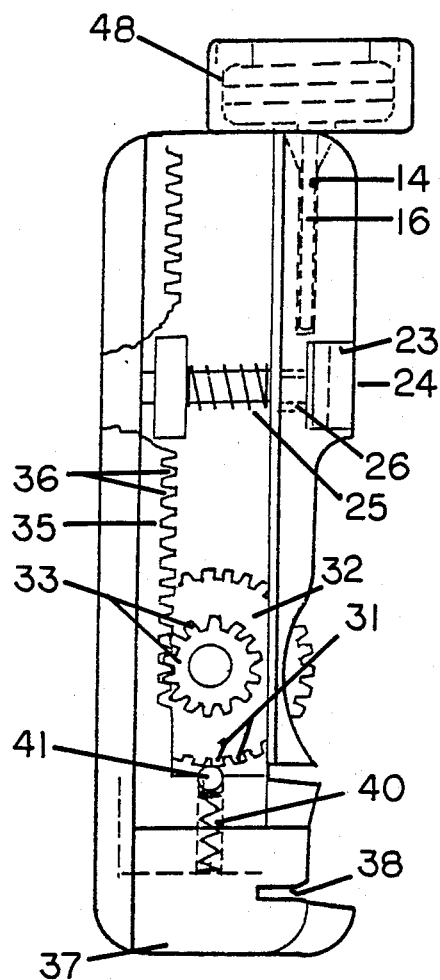
FIG. 4
FIG. 5
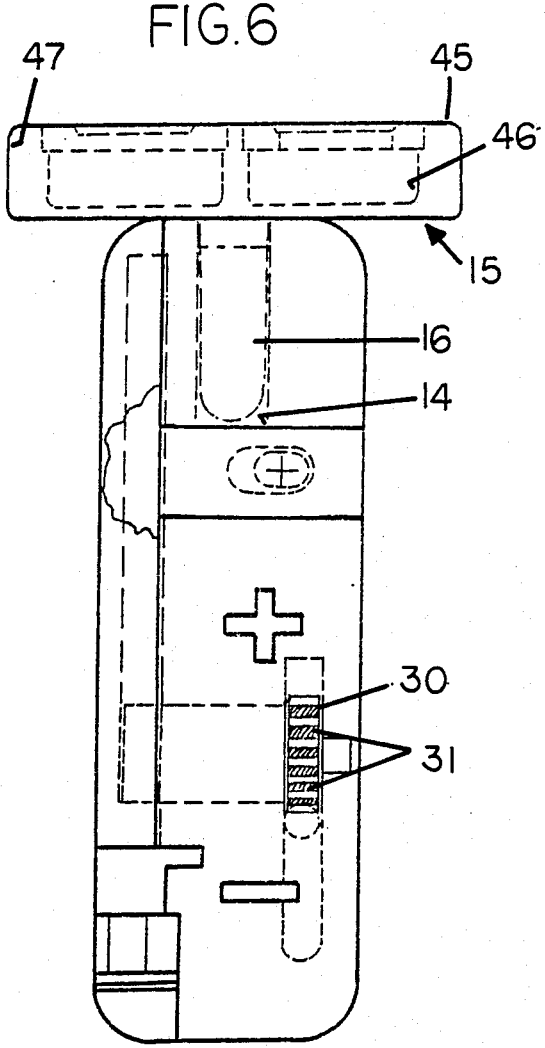
FIG. 6

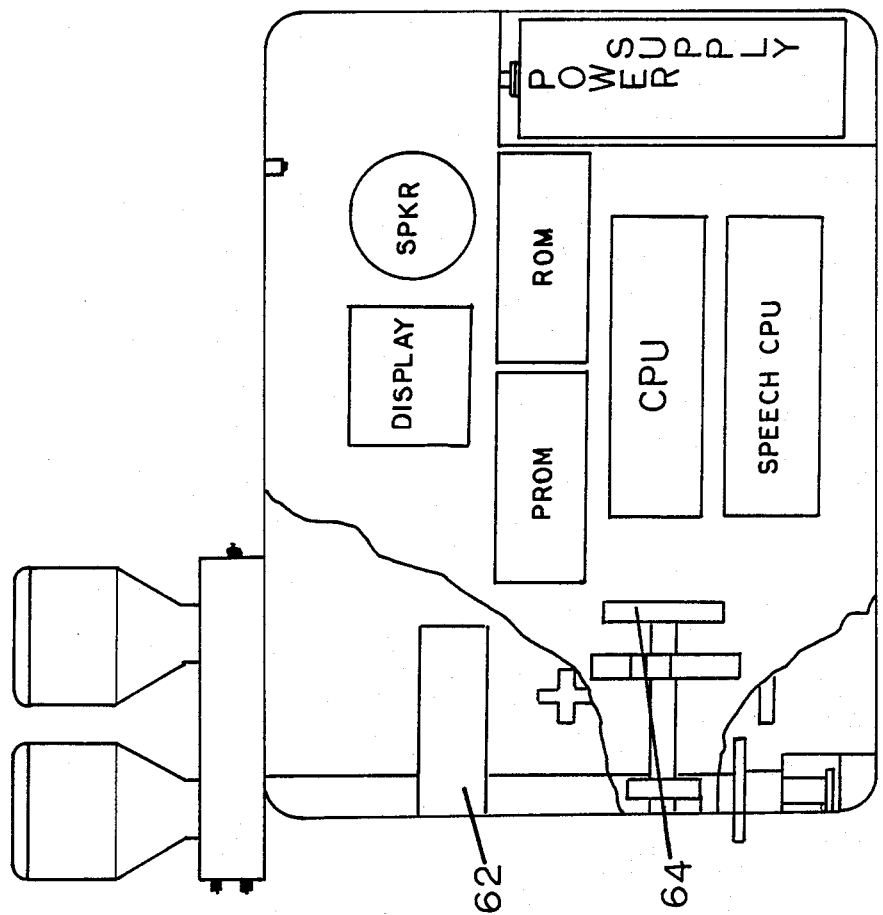
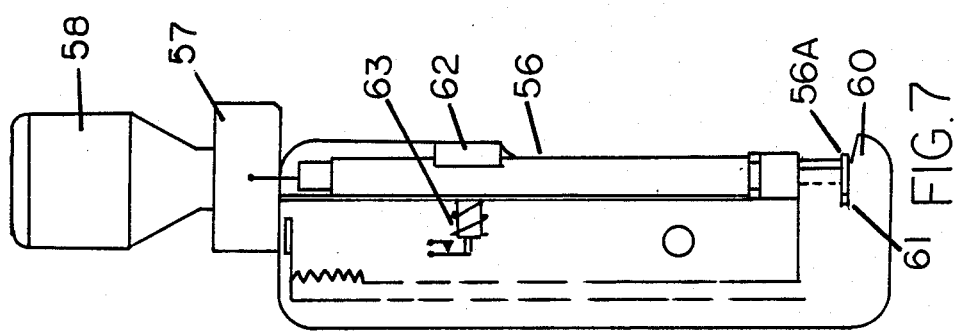

FILLING DEVICE WITH SOUND INDICATOR FOR FILLING INJECTION SYRINGE

BACKGROUND OF THE INVENTION

This invention relates to a new and improved filling device for filling an injection syringe, the device providing a sound indicator to enable the user to accurately determine the amount of liquid medicine drawn into the syringe. The filling device of this invention is particularly suited for insulin injection by patients with impaired vision.

Various prior publications concerning these devices are to be found in U.S. Pat. Nos. 3,840,011; 3,935,883; 3,965,945; 4,018,223; 4,489,766; 4,501,306; and, 4,617,016. However, these prior art devices tend to be complicated and expensive. Moreover, many of these devices do not deal effectively with the problem of vision impaired persons who are frequently unattended and must fend for themselves with the danger of an overdose, underdose, or the use of an incorrect medicine.

Obviously, it would be very beneficial for a vision impaired person to be able to use a simple, safe and inexpensive assembly for a needle injector with little training, and which would enable independent injection by the user.

THE INVENTION

According to the invention, the filling device for filling a syringe injector provides a gear driven support for the injector and a bias driven element such as a ball bearing which is forced into contact with the gear as it is rotated by the user, and makes a distinct clicking sound as it contacts each gear element. This clicking sound is equivalent to a small and specific medicinal doseage which the user can translate into the correct prescribed insulin (or other medicinal) doseage. This sound is also transmitted to the user as a vibration.

If the user feels a miscount has been made, the liquid medicine can be reinjected into the attached medicine container, and the filling procedure is then repeated. This represents a simple safety feature, and also avoids discarding the medicine unnecessarily.

Instead of a mechanical clicking device, an electrical or electronic signalling system may be used, which may include an audible tone, an artificial voice counter, etc.

BRIEF DESCRIPTION OF THE DRAWINGS

FIG. 4 is an external view in side elevation, partly broken away, showing the internal components of the device;

FIG. 5 is an external end view of FIG. 4;

FIG. 6 is an external view in side elevation of the device showing the attachment means of the liquid medicine containers;

FIG. 7 is an external view in side elevation, and partly in section showing the device adapted for use with a microprocessor controlled synthetic voice counting output;

FIG. 8 is a diagrammatic representation of the system flow diagram employing the microprocessor control of FIG. 7; and, FIG. 9 is a system flow diagram of the artificial voice synthesizer employed in conjunction with the device of this invention to obtain a synthetic voice count output.

DESCRIPTION OF THE PREFERRED EMBODIMENTS

Figure 1:
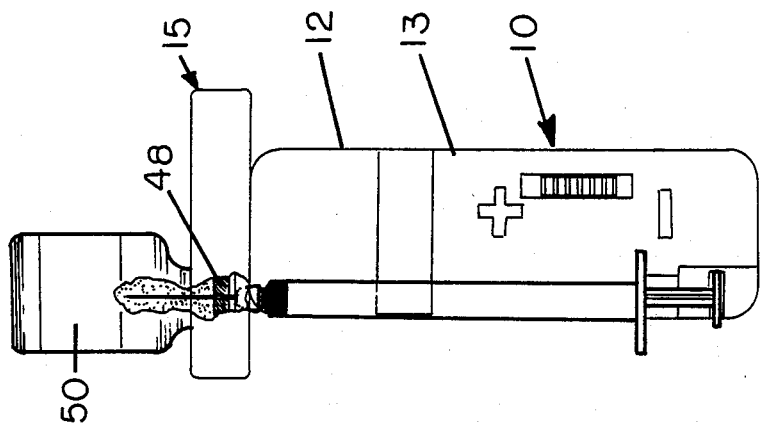
FIG. 1 is an external view in side elevation showing the assembled device prior to filling.

The injection device 10 of this invention for filling an injection syringe 11 is shown in FIGS. 1-6, in the embodiment used with a mechanical sound indicator.

The injection device is constructed typically of an injection molded plastic exterior case 12 having a removeable cover 13. The upper end of the cover defines a slot 14 into which is fitted a bottle holder 15 attached to an extension arm 16, and which will be described in more detail, infra. The lower portion of the cover 13 is slotted 17 to enable interfitting with the fingergrip 18 of a syringe 19 having a barrel portion 20, stem 21, and finger pad 22. The cover 13 is slotted 23 to receive a locking arm 24 which is biased by a spring 25 through bore hole 26 to enable the locking arm to partly wrap around and engage the barrel portion 20 of the syringe 19.

The cover 13 is slotted 30 to expose gear teeth 31 of a a gear wheel 32, and a "+" and "−" signs are embossed molded onto the face of the cover, thereby enabling a vision impaired user to rotate the gear towards the + sign and load the syringe. If the user looses count of the gear clicks, the syringe can be unloaded by moving the gear in the direction of the "−" sign.

The gear wheel 32 is rotatably mounted within the exterior case 12 and includes an internal gear element defining gear teeth 33. A linear gear element 35 is mounted within the case 12, and includes gear teeth 36, and an attached end member 37, which is slotted 38 to enable interfitting with the finger pad 22 of the syringe stem 21. The gear teeth 36 engage the gear teeth 33 of the internal gear element.

The interior of the case 12 defines a slot 40 into which is fitted a spring loaded bearing 41 that is biased agaist the gear teeth 31. When each individual gear tooth 31 contacts the bearing 41, it will make a distinctly audible click, which as noted, can then be translated into a prescribed patient doseage.

In the assembled position shown in FIG. 1, the unfilled syringe 19 is supported by the injection device 10 by means of the locking arm 24 and interfitting slot 17 of the cover 30 and slot 38 of the linear gear element 35.

The bottle holder 15 provides a base 45 having recess bores 46, 47 lined with rubber washer elements, one washer 48 being shown; these washers secure bottles 49, 50 in place. The base 45 defines a single protrusion 51 at one end, and double protrusions 52, 53 which are embossed thereon to correctly categorize the type of medicine bottle 49, 50 as contained in each recess bore. In the case of insulin, the bottles are correctly identified at the pharmacy by suitable labelling, rubber band, etc. As shown in FIG. 5, the bottle holder 15 can be switched around, and enable a second bottle 50 (or 49) to be used. This is particularly helpful to insulin users, who may be vision impaired, and whose medicinal needs include the need to mix two solutions of insulin in the syringe.

Figure 2:
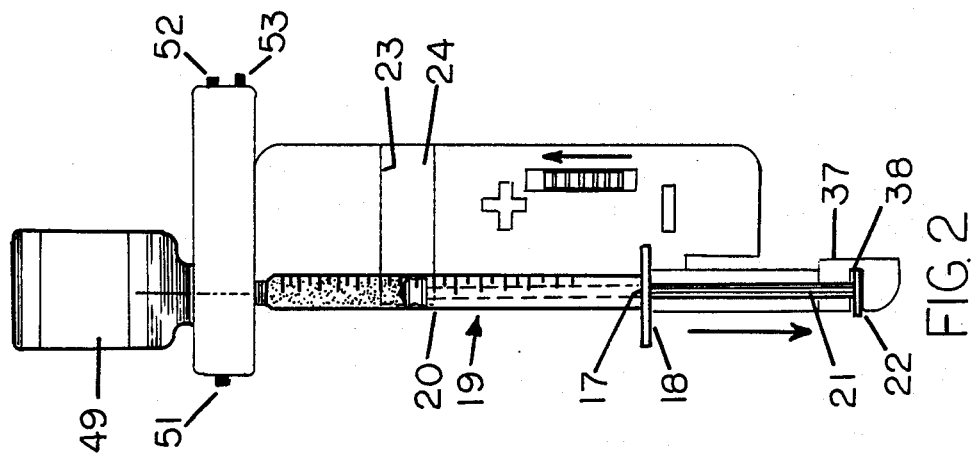
FIG. 2 is an external view in side elevation showing the device during filling of liquid medicine from an attached container.
Figure 3:
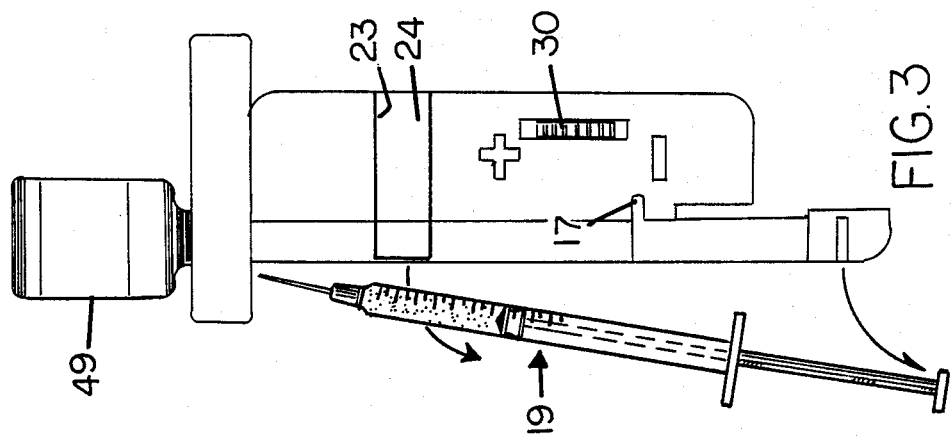
FIG. 3 is an external view in side elevation showing the device following removal of a filled syringe therefrom.

Following insertion of the syringe 19 into the injection device 10 and bottle 49, as shown in FIG. 1, the gear wheel 32 is rotated in the "+" direction to load the syringe, as shown in FIG. 2. The user must carefully count the number of clicks, which correspond to a prescribed injection. If the user feels the count is incorrect, the liquid may be reinjected into the bottle without loss of medicine. The syringe is then removed from the injection device and bottle, in the direction shown by the arrows, as illustrated in FIG. 3. For purposes of illustration, the bottle 49 and bottle holder are shown attached to the device 10, but in actual practice, these two components are removed prior to detaching the syringe; in addition, the device is oriented in a horizontal manner when the syringe is detached, rather than in an upright manner, as shown.

Figure 9:
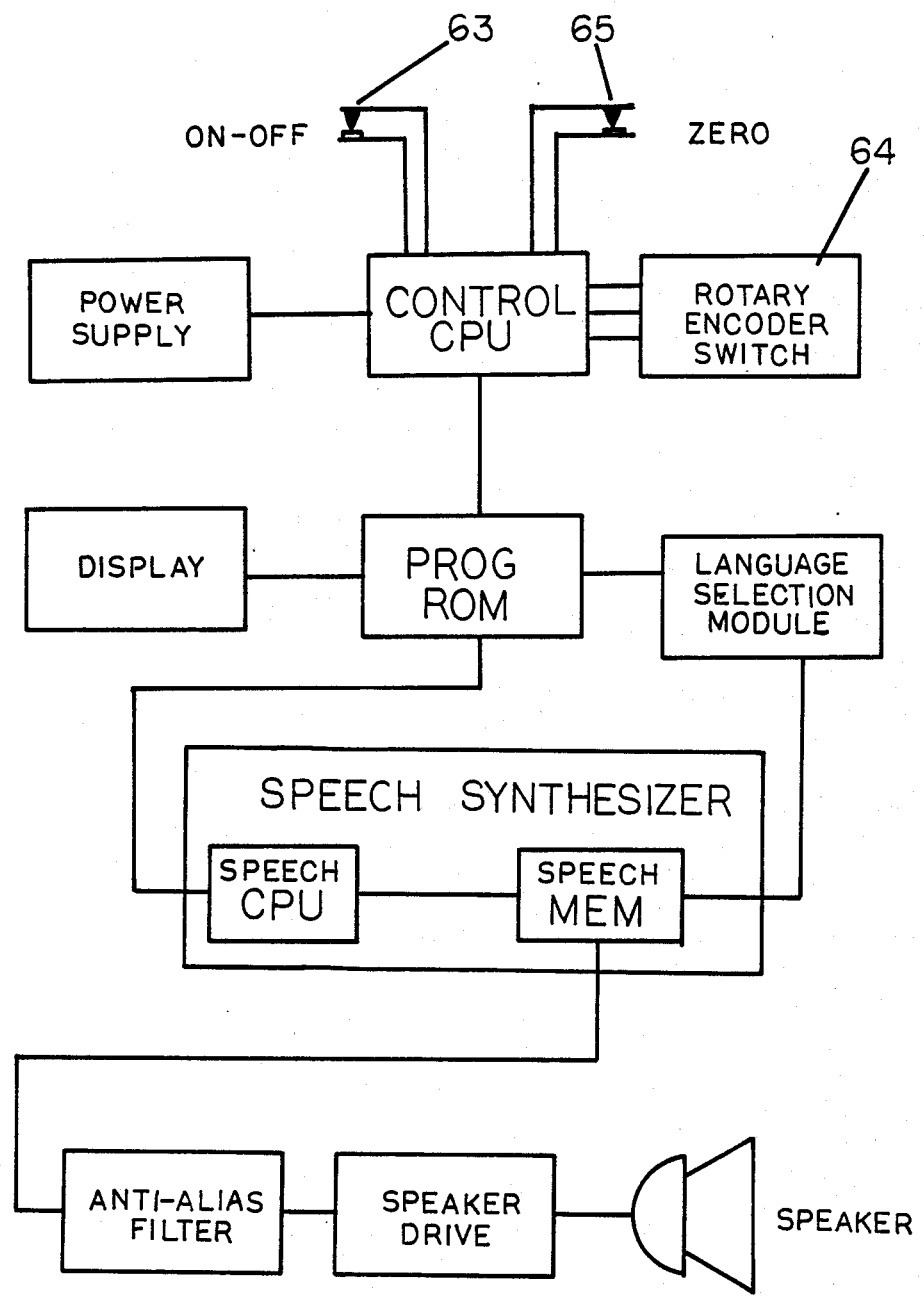

FIGS. 7-9 illustrate an embodiment of this invention, used in conjunction with a microprocessor and artificial speech unit, for enabling vision impaired persons to use the filling device, without requiring a visual observation of the syringe or filling device.

The filling device shown in FIGS. 7 and 8 requires a larger exterior case than for the embodiment shown in FIGS. 1-6 in order to accommodate the electronic components, but the mechanical features are essentially the same. In FIG. 7, the device is shown mounting a syringe 56, including a finger pad 56 A, a container holder 57, and attached liquid medicine container 58. The syringe is attached to the device by means of a spring loaded locking arm 62 located medially of the syringe, and attached, moveable end member 60 of a linear gear rack which provides an interfitting slot 61 for the finger pad 56 A of the syringe. A switch 63 is used to turn the device on and off, when the locking arm 62 is opened or closed.

A rotary encoder switch 64 is mounted on gear wheel 32, and actuates the end member 60 to fill the syringe when moved in the "+" or "—" directions, respectively. The encoder is connected to the CONTROL CPU (an 8-bit microprocessor-U8031), and each gear tooth movement of the encoder in the "+" or "—" direction will produce an appropriate signal in the CONTROL CPU. A switch 65 is employed to set the CONTROL CPU at the zero reading when the syringe 56 is inserted into the device and adjusted to the closed position, shown in FIG. 9.

A programmable read-only-memory (PROG ROM) employing a 64K EPROM (2764 chip) contains the program voice and LCD readouts for the system. If desired, a DISPLAY produces the LCD visual readout (from an ICM 7211) alone, or in conjunction with the audio speech synthesizer, and enables the user to double check the liquid uptake by the syringe.

A LANGUAGE SELECTION MODULE is adapted to provide an appropriate language form (e.g. English, French, Spanish, German, etc.) for the audio synthesizer. Signals from the PROG ROM and LANGUAGE SELECTION MODULE are fed to a SPEECH CPU (MM54104N) and speech memory (SPEECH MEM-MM52164-SSR1) in the SPEECH SYNTHESIZER section to produce an appropriate synthesized voice output corresponding to the liquid uptake by the syringe 56. The SPEECH MEM section is programmed by the 2764 EPROM to recall the latest reading and to feed this information to the SPEECH CPU for output to a SPEAKER via an anti-alias filter and a SPEAKER DRIVE (LM 386N).

The device of this invention enables a user to employ common components and mechanisms to obtain a mechanical (audible clicking) sound, an equivalent electrically produced audible tone signel, or a voice synthesized readout or tone, etc. In all cases, the user can eject excess liquid medicine back into the medicine bottle if there is any doubt concerning the accuracy of the liquid uptake reading.

The device of this invention has the capability of being programmable to effect preset dosages from each of the liquid medicine bottles which are different, and such dosages can be readily varied.

I claim:

1. A filling device for a syringe, including barrel and stem portions, comprising a case portion, and including:
   i. movable holding means for releasably securing the stem portion of the syringe, and adapted to load or unload the syringe by movement of the stem portion;
   ii. a linear gear, including gear teeth attached to the holding means, and adapted to move the holding means;
   iii. a rotatable gear mounted by the case portion, the rotatable gear defining manually actuable gear teeth, the rotatable gear including gear teeth for engaging and actuating the gear teeth of the linear gear;
   iv. a sounding element adapted to be biased against the manually actuable gear teeth of the rotatable gear; and,
   v. a locking arm mounted on the filling device and adapted to secure the syringe against movement when the syringe stem is moved to load or unload the syringe, the locking arm being adapted to release the syringe after loading; and, means for detachably mounting to the filling device a bottle containing liquid medicine for loading or unloading by the syringe; whereby:
   vi. movement of the linear gear in one direction causes the holding means to load the syringe with liquid medicine from the medicine bottle, and movement of the linear gear in an opposite direction causes the syringe to unload liquid medicine into the bottle; and,
   vii. manual movement of the rotatable gear produces a sound from the sounding element due to contact with an individual gear tooth of the manually actuable gear teeth which coincides with an increment of movement of the rotatable gear, each sound being equivalent to a predetermine amount of liquid medicine loaded by the syringe.

2. The filling device of claim 1, comprising an assembly of the device and a syringe.

3. The filling device of claim 2, in which the assembly includes a bottle holder and bottle of liquid medicine mounted thereon.

4. The filling device of claim 3, employing two different bottles of liquid medicine, and the bottle holder is embossed with indicia to differentiate between each of said bottles.

5. The filling device of claim 4, in which the said bottle holder is reversable in position on the filling device, thereby enabling mixing of the medicines.

6. The filling device of claim 1, in which the sounding element is a ball bearing.

7. The filling device of claim 1, in which the stem portion of the syringe interfits with the moveable holding means, and is moveable therewith, and the syringe barrel is secured by the locking arm against movement, when the stem portion is moved.

8. The filling device of claim 1, in which the rotatable gear defines a peripheral edge and said manually actuable gear teeth defined on the peripheral edge, and a commonly mounted gear element providing said gear teeth for engaging the gear teeth of the linear gear.

* * * * *